US009724017B2

United States Patent
Baloa Welzien et al.

(10) Patent No.: US 9,724,017 B2
(45) Date of Patent: Aug. 8, 2017

(54) RESPIRATORY CYCLE PATIENT VENTILATION FLOW LIMITATION DETECTION

(71) Applicant: Breathe Technologies, Inc., Irvine, CA (US)

(72) Inventors: Leonardo Alberto Baloa Welzien, Lake Forest, CA (US); Samir S. Ahmad, San Diego, CA (US)

(73) Assignee: Breathe Technologies, Inc., Irvine, CA (US)

( * ) Notice: Subject to any disclaimer, the term of this patent is extended or adjusted under 35 U.S.C. 154(b) by 398 days.

(21) Appl. No.: 13/935,362

(22) Filed: Jul. 3, 2013

(65) Prior Publication Data

US 2015/0011905 A1    Jan. 8, 2015

(51) Int. Cl.
| | |
|---|---|
| *A61M 16/00* | (2006.01) |
| *A61B 5/085* | (2006.01) |
| *A61B 5/087* | (2006.01) |
| *A61B 5/00* | (2006.01) |
| A61M 16/06 | (2006.01) |
| A61M 16/08 | (2006.01) |

(Continued)

(52) U.S. Cl.
CPC .............. *A61B 5/085* (2013.01); *A61B 5/087* (2013.01); *A61B 5/4836* (2013.01);
(Continued)

(58) Field of Classification Search
CPC ........................ A61M 16/06; A61M 2230/40
See application file for complete search history.

(56) References Cited

U.S. PATENT DOCUMENTS

| | | | |
|---|---|---|---|
| 4,776,333 A | 10/1988 | Miyamae | |
| 5,490,502 A * | 2/1996 | Rapoport | ............. A61B 5/0002 128/204.21 |

(Continued)

FOREIGN PATENT DOCUMENTS

WO        0218002        3/2002

OTHER PUBLICATIONS

MathVids, Cartesian Graphs and the Second Derivative, 2011, Web Video, Retrieved from: http://mathvids.com/lesson/mathhelp/1353-cartesian-graphs-and-the-second-derivative.*

(Continued)

*Primary Examiner* — Jacqueline Cheng
*Assistant Examiner* — Angeline Premraj
(74) *Attorney, Agent, or Firm* — Stetina Brunda Garred & Brucker

(57) ABSTRACT

A single respiratory cycle flow limitation detection method is disclosed. A patient gas delivery signal is received from one or more sensors in pneumatic communication with a ventilation source and a patient ventilation interface to a patient airway. The patient gas delivery signal is representative of a measure of therapeutic gas being delivered to the patient airway at a given time instant, and spans the single patient respiratory cycle. A second derivative of the patient gas delivery signal is generated and a total number of zero crossings therein are counted. These zero crossings are representative of an inflection change in the patient gas delivery signal. A flow limitation indication corresponding to the identified flow limitation is generated when there are at least two zero crossings in the second derivative of the patient gas delivery signal. An angle of deformation representing early, late, or mid-cycle obstruction onsets is generated.

9 Claims, 4 Drawing Sheets

(51) Int. Cl.
*A61M 16/20* (2006.01)
*A61M 16/10* (2006.01)

(52) U.S. Cl.
CPC .......... *A61B 5/7278* (2013.01); *A61B 5/7282* (2013.01); *A61M 16/0051* (2013.01); *A61M 16/0069* (2014.02); *A61M 16/06* (2013.01); *A61M 16/0858* (2014.02); *A61M 16/107* (2014.02); *A61M 16/205* (2014.02); *A61M 16/206* (2014.02); *A61M 2016/0027* (2013.01); *A61M 2016/0039* (2013.01); *A61M 2205/42* (2013.01); *A61M 2205/7545* (2013.01)

(56) References Cited

U.S. PATENT DOCUMENTS

| | | | |
|---|---|---|---|
| 6,029,665 | A | 2/2000 | Berthon-Jones |
| 6,138,675 | A | 10/2000 | Berthon-Jones |
| 7,438,073 | B2 * | 10/2008 | Delache ............... A61M 16/00 128/204.23 |
| 8,025,052 | B2 | 9/2011 | Matthews et al. |
| 2002/0040192 | A1 | 4/2002 | Prutchi |
| 2005/0031322 | A1 | 2/2005 | Boyle et al. |
| 2007/0113856 | A1 * | 5/2007 | Acker ............... A61M 16/0051 128/207.14 |
| 2008/0029096 | A1 | 2/2008 | Kollmeyer et al. |
| 2011/0197885 | A1 * | 8/2011 | Wondka ................... A61B 5/03 128/204.22 |
| 2011/0203588 | A1 * | 8/2011 | Armitstead ....... A61M 16/0051 128/204.21 |
| 2011/0230779 | A1 * | 9/2011 | Titchener ............... A61B 5/087 600/538 |

OTHER PUBLICATIONS

International Search Report and Written Opinion for International Application No. PCT/US2014/044705, Oct. 17, 2014, 9 Pages.
Extended European Search Report for EP 14 820 475.3, mailed on Feb. 2, 2017.

* cited by examiner

RESPIRATORY CYCLE PATIENT VENTILATION FLOW LIMITATION DETECTION

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

The present disclosure relates generally to the treatment of respiratory and cardiovascular disorders with a mechanical ventilator, and more particularly, to single respiratory cycle patient ventilation flow limitation detection.

2. Related Art

The respiration system of the human body provides needed oxygen intake, oxygen/carbon dioxide exchange, and carbon dioxide expulsion functions, each of which involves the lungs. In this regard, the lungs function as a gas-exchanging organ in which inhaled oxygen is passed to the blood, and collected carbon dioxide is passed from the blood to the air. Additionally, the lungs function as a respiratory pump that transports oxygen-rich air into the lungs, and the carbon dioxide-rich air out of the lung. The breathing center in the brain, central and peripheral nerves, the osseous thorax and the breathing musculature as well as free, stable respiratory paths are necessary for a correct functioning of the respiratory pump.

There are a variety of conditions that adversely affect the respiratory function of a person, particularly during sleep. Among these is apnea, where airflow to the lungs is interrupted and the normal respiratory cycle is broken. The stopped airflow or apnea may result from a failure of the basic neurological controls over breathing, with no breathing effort being expended. This type of apnea is known as central sleep apnea (CSA). Alternatively, the apnea may result from a constriction in the upper airway that also interrupts normal respiration, but while the patient exerts breathing effort. This type is known as obstructive sleep apnea (OSA). Where the patient's breathing efforts overcome the obstruction yet there is a significant reduction in airflow, there is understood to be hypopnea. There are repetitive pauses in breathing that may extend in duration up to half a minute. These conditions, at the very least, result in disruptions to sleep cycles because the patient is aroused to a waking state in an attempt to achieve proper respiration, leading to daytime drowsiness and fatigue as a consequence of reduced blood oxygen saturation and/or increased blood carbon dioxide concentration. In more severe cases, blood oxygen saturation may be so reduced (a condition referred to as hypoxemia), or the blood carbon dioxide concentration may be so high (a condition referred to as hypercapnia) that morbidity may be result.

In order to retain the patient's airway and ensure normal, uninterrupted breathing during sleep, continuous positive airway pressure (CPAP) therapy may be prescribed. Generally, CPAP involves the application of positive pressure to open the patient's airway to prevent its collapse, as would otherwise occur during apnea. In a basic implementation, CPAP therapy applies a constant pressure that is not tied to the patient's normal breathing cycle. The positive airway pressure is desired in the inspiratory phase when the pressure differences between the lungs and the nose contribute to the collapse of the intermediate airway. Such implementations were typically uncomfortable for the patient as there were differing augmentation needs depending on the degree of obstruction, and the relative point within the breathing cycle. Accordingly, CPAP systems with varied pressure augmentation based on the detection of full or partial obstruction of the airway were developed.

Existing flow limitation detection techniques are understood to be based upon the understanding that partial airway obstructions as with OSA result in mid-inspiratory flow limitation. One technique involves a calculation of the index of a partial obstruction through a shape factor, as set forth in U.S. Pat. No. 6,029,665 as well as U.S. Pat. No. 6,138,675 both to Berthon-Jones. Another technique involves a calculation of the degree of flow limitation defined as a series of shape detection factors, including a sinusoidal index, a flatness index, respiratory effort index, and relative flow index.

All of these conventional methods, however, are deficient since multiple indices must be compared to a predefined threshold in order to evaluate whether a flow limitation corresponding to an obstructed respiration condition exists. Accordingly, there is a need in the art for an improved method for single respiratory cycle patient ventilation flow limitation detection.

BRIEF SUMMARY

A single respiratory cycle flow limitation detection method in accordance with various embodiments of the present disclosure utilize a second derivative of a signal corresponding to patient flow during inspiration. The method may begin with receiving a patient gas delivery signal from one or more sensors that is in pneumatic communication with a ventilation source and a patient ventilation interface to a patient airway. The patient gas delivery signal may be representative of a measure of therapeutic gas being delivered to the patient airway at a given time instant. Furthermore, the patient gas delivery signal may span the single patient respiratory cycle. The method also includes generating a second derivative of the patient gas delivery signal, and then counting a total number of zero crossings therein. The zero crossings of the second derivative of the patient gas delivery signal may be representative of an inflection change in the patient gas delivery signal. Furthermore, the method may include generating a flow limitation indication that corresponds to the identified flow limitation. In order for this to occur, the total of the zero crossings in the generated second derivative of the patient gas delivery signal is at least two. Another aspect of the method contemplates generating an angle of deformation that defines whether there is an early obstruction, a late obstruction, or a mid-cycle obstruction so that treatment can be adjusted accordingly.

Certain other embodiments of the present disclosure contemplate respective computer-readable program storage media that each tangibly embodies one or more programs of instructions executable by a data processing device to perform the foregoing method.

In another embodiment of the present disclosure, a respiratory assistance device is contemplated. The device may include a variable speed blower with an output, and a patient ventilation interface configured for fitment on a patient respiratory passageway. Additionally, the device may include a gas passage conduit that couples the output of the blower to the patient ventilation interface. The device may also include one or more sensors detecting a gas delivery value through the gas passage conduit. The sensor may further generate a patient gas delivery signal in response to the measured gas delivery value. The respiratory assistance device may also include a controller that is in communication with the pressure sensor and the flow sensor. A flow limitation indication may be generated in response to a detection of at least two zero crossings in a second derivative of the patient gas delivery signal. Again, the zero crossings may be representative of an inflection change in the patient flow signal. An angle of deformation is generated from a first of the inflection changes and a second of the inflection changes, with a negative value representing an early obstruction onset, a positive value representing a late obstruction onset, and an approximate zero value representing symmetrical or mid-cycle obstruction onset.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

The detailed description set forth below in connection with the appended drawings is intended as a description of the presently preferred embodiment of flow limitation detection, and is not intended to represent the only form in which the presented embodiments may be developed or utilized. It is further understood that the use of relational terms such as first and second and the like are used solely to distinguish one from another entity without necessarily requiring or implying any actual such relationship or order between such entities.

Figure 1:
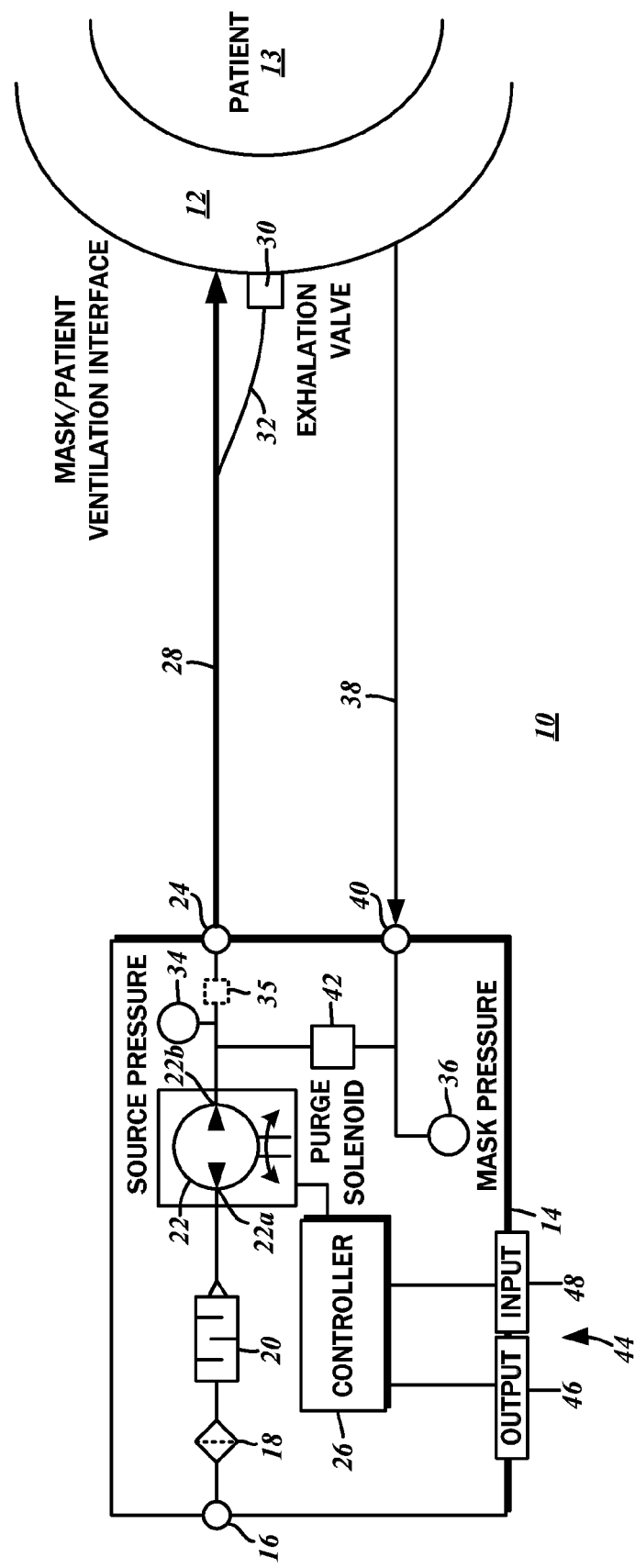
FIG. 1 is a block diagram showing the various components of a patient ventilation apparatus in accordance with various embodiments of the present disclosure.

The block diagram of FIG. 1 illustrates an exemplary respiratory assistance device 10 in which various embodiments of the present disclosure may be implemented. There is a mask or patient ventilation interface 12, and a ventilation unit 14. The patient ventilation interface 12 is understood to be an apparatus such as a full-face mask or a nasal pillows mask that can be placed in direct gas flow communication with the upper respiratory tract, i.e., the nasal cavity and/or the oral cavity, of a patient 13. It will be appreciated that other apparatuses that so interface the respiratory tract of the patient 13 to the ventilation unit 14 may be substituted without departing from the scope of the present disclosure.

The ventilation unit 14 generates a flow of breathing gas that is delivered to the patient via the patient ventilation interface 12. The breathing gas may be ambient air, a combination of ambient air enriched with oxygen, or any other suitable mixture of gas appropriate for treating the patient. Those having ordinary skill in the art will recognize the variety of options for mixing breathing gasses before delivery to the patient. In further detail, the ventilation unit 14 includes a first inlet port 16, through which ambient air is drawn. The first inlet port 16 is in communication with an inlet filter 18 that removes particulates and other contaminants from the breathing gas that is ultimately delivered to the patient. Optionally, in line with the inlet filter 18 is a sound suppressor 20 that reduces the sound of gas flow through the ventilation unit 14.

The force needed for drawing the ambient air through the first inlet port 16, the inlet filter 18, and the sound suppressor 20 is provided by a ventilation source 22, which may be a centrifugal fan, blower, or any other suitable device that generates gas flow and pressure suitable for CPAP treatment in accordance with the present disclosure. The ventilation source 22 has an inlet port 22a coupled to the sound suppressor 20, and an outlet port 22b that is in gas flow communication with an outlet port 24 of the ventilation unit 14. The ventilation source 22 is driven electrically and its actuation is governed by a controller 26, which implements the various functionalities described in further detail below.

The flow of breathing gas that is output from the ventilation source 22 is passed through the outlet port 24 to a gas conduit 28 that is in coupled to the aforementioned patient ventilation interface 12. The gas conduit 28 is understood to be a plastic tube having a predetermined inner diameter such as 22 mm or smaller, though any other conduit of suitable material and construction may be utilized. The patient ventilation interface 12 in accordance with various embodiments of the present disclosure also includes a piloted exhalation valve 30 that is selectively actuated depending on the pressure differential between the patient ventilation interface 12 and the ventilation unit 14. The exhalation valve 30 is connected to a pilot line 32 that branches from the gas conduit 28. A pressure difference is generated between the patient ventilation interface and the exhalation valve, such that it is closed during inspiration and opened during expiration. It will be appreciated that the specifics of the patient ventilation interface 12, including the piloted exhalation valve 30 thereof, are presented by way of example only and not of limitation. Any other suitable patient ventilation interface 12, including those that may be utilized in conjunction with different variations of the ventilation unit 14, may be substituted without departing from the scope of the present disclosure.

In one embodiment of the presently contemplated ventilation system 10, there are dual pressure sensors, including a source pressure sensor 34 and a patient interface pressure sensor 36. The source pressure sensor 34 is disposed within the ventilation unit 14, and monitors the pressure at the ventilation source output port 22b. The patient interface pressure sensor 36 is also physically disposed within the ventilation unit 14, but is in direct gas flow communication with the patient ventilation interface 12 over a pressure sensing line 38 that is connected to a sensor inlet port 40 of the ventilation unit 14. When the ventilation unit 14 is operating, gas pressure within the pressure sensing line 38 as well as the gas conduit 32 may be connected to deliver a purge flow to clear the pressure sensing line 38. This can be done through a purge solenoid 42 connected to both. The purge can be continuous or intermittent according to the patient's breathing phase or pressure difference between the valve pressure and the patient interface pressure. Optionally, either in addition to the dual pressure sensors 34, 36, or as a replacement for the source pressure sensor 34, a flow rate sensor 35 may be in pneumatic communication with the output 22b of the ventilation source 22 and the gas conduit 28 to measure airflow therethrough.

The sequence and timing of delivering gas flow to the patient 13 are governed by the specific treatment modalities that utilize feedback data from the pressure sensors 34, 36 and/or the flow rate sensor 35. The setting of options relating to the treatment modalities, along with the starting and stopping of treatment is possible via a user interface 44 coupled to the controller 26, which includes an output or display interface 46, as well as an input interface 48.

As mentioned above, various embodiments of the present disclosure contemplate a method for identifying flow limitation from a single patient respiratory cycle. With reference to the flowchart of FIG. 2, the method begins with a step 100 of receiving a patient gas delivery signal from the flow sensor 35 or the pressure sensors 34, 36. The patient gas delivery signal is understood to be representative of some measure, i.e., volume or pressure of therapeutic gas (in liters per minute or in cm H$_2$O, respectively) that is being delivered to the patient airway at a given time instant. The patient gas delivery signal in such embodiment is understood to represent a flow rate. In some cases, the patient gas delivery signal may be based upon an approximation of pressure differences as measured by the pressure sensor 34, 36. It is also possible to determine this value based upon a single one of the pressure sensors 34, 36. In such embodiments, the patient gas delivery signal represents a pressure value.

Figure 3A:
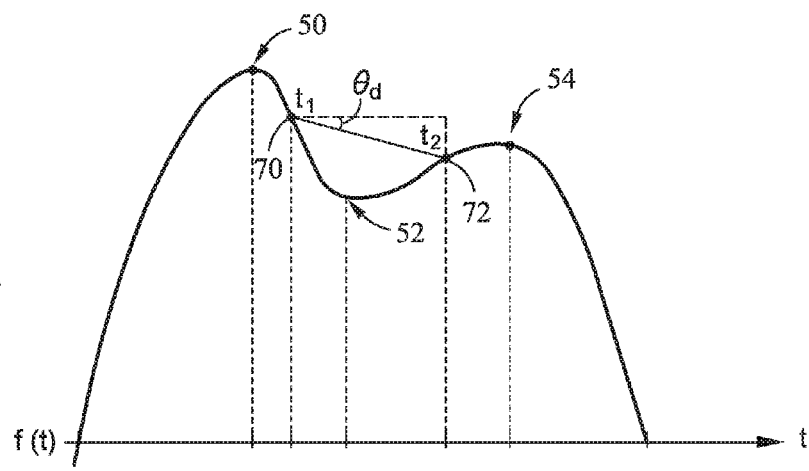
FIG. 3A-3C are graphs plotting exemplary patient airflow, a first derivative of the patient airflow, and a second derivative of the patient airflow, respectively, during inspiration.

The graph of FIG. 3A shows a time-magnitude plot of one such exemplary patient gas delivery signal over one inspiratory cycle. It will be recognized that there is an initial rapid rise to a first peak 50, followed by a rapid decrease to a valley 52 (though there continues to be some degree of flow), and then a gradual rise to a second peak 54 as patient breathing effort slightly overcomes the obstruction, then another reduction to zero flow as the inspiration cycle is completed. The plot is understood to be an approximation, as an actual measured signal may have significant fluctuations. In order to minimize these fluctuations, it is also possible to utilize a band-pass filter to eliminate high and low frequency noise. Thus, there may additionally be a step 101 of filtering the patient gas delivery signal. One implementation contemplates a pass band of 0.01 Hz to 10 Hz. Alternative configurations that best optimize the patient gas delivery signal may be substituted without departing from the scope of the present disclosure.

Figure 3B:
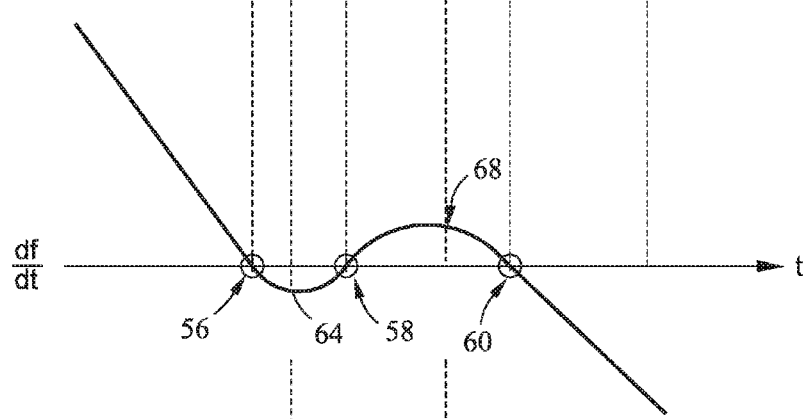

The graph of FIG. 3B is a plot of the first derivative $$\frac{df}{dt}$$

of the patient gas delivery signal, and has zero crossing points corresponding to the aforementioned points of interests, namely, the first peak 50, the valley 52, and the second peak 54. In further detail, there is a first zero crossing 56 corresponding to the first peak 50, a second zero crossing 58 corresponding to the valley 52, and a third zero crossing 60 corresponding to the second peak 54. As will be recognized, the first derivative represents the degree of change in the airflow at a given time instant, and is understood to be zero when there is a transition between a positive rate of change to a negative rate of change in airflow, and vice versa. Although in the illustrative example there are three first derivative zero crossings, patient gas delivery signals need not be limited thereto. It is possible for there to only be one, or more than three, and so the first derivative is unsuitable for determining the existence of flow limitation.

Figure 2:
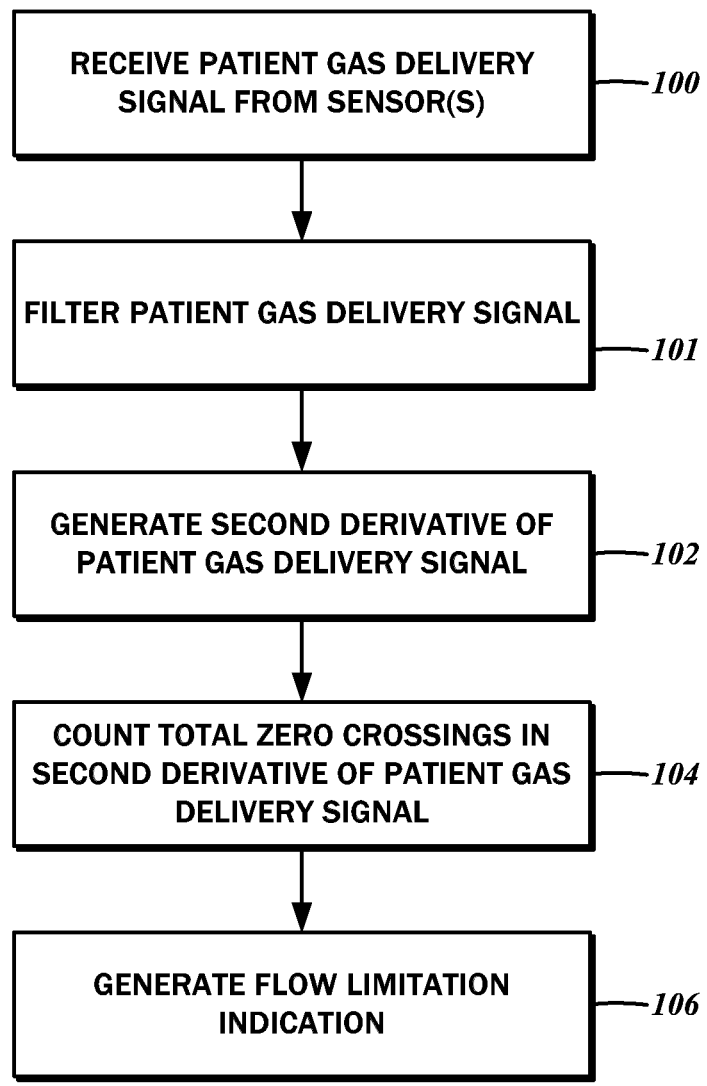
FIG. 2 is a flowchart of one method for flow limitation detection.
Figure 3C:
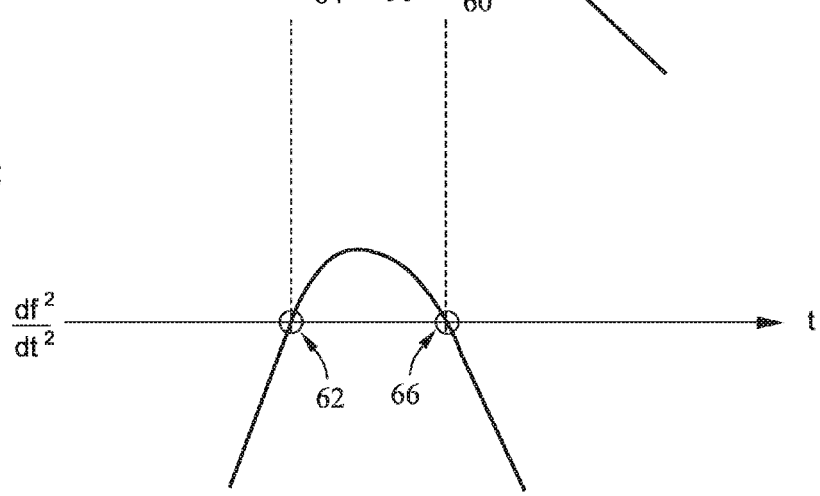

Referring to the flowchart of FIG. 2, the method thus continues with a step 102 of generating a second derivative $$\frac{df^2}{dt^2}$$

of the patient gas delivery signal, an example of which is shown in FIG. 3C. Simultaneously referring to the graph of FIG. 3B, the second derivative defines a first zero crossing 62 that corresponds in time to a minimum or valley 64 between the first zero crossing 56 and the second zero crossing 58 of the first derivative. Additionally, the second derivative defines a second zero crossing 66 that corresponds in time to a maximum or peak 68 between the second zero crossing 58 and the third zero crossing 60 of the first derivative. The second derivative zero crossings are understood to be representative of an inflection change in patient airflow. That is, a positive or negative derivative reduces its rate of increase or decrease, respectively.

The method further includes a step 104 of counting the total of zero crossings in the second derivative of the patient gas delivery signal. It is understood that the zero crossings may be counted for any duration of time. When there is a flow limitation, as shown in FIG. 3C, there are at least two zero crossings. An indication thereof is generated in accordance with step 106.

Another aspect of the method for flow limitation detection involves the evaluation of symmetry with respect to patient airflow. In further detail, additional insight as to when in the inspiration cycle, that is, before peak flow, after peak flow, or during peak flow can be exploited to optimize treatment. Referring to the graphs of FIG. 3A and 3C, this is determined by an angle of deformation based upon a first gas delivery value corresponding to a first time instant 70 of a first one of the zero crossings in the second derivative, and a second gas delivery value 72 corresponding to a second time instant of a second one of the zero crossings in the second derivative. More particularly, $t_1$ is where $$\frac{d^2 f(t_1)}{dt^2} = 0,$$

and $t_2$ is where $$\frac{d^2 f(t_2)}{dt^2} = 0.$$

The angle of deformation $\theta_d$ is given by $$\tan^{-1} \frac{f(t_2) - f(t_1)}{t_2 - t_1}.$$

If $\theta_d$ is approximately zero, it is understood to correspond to a symmetrical response. If $\theta_d$ is less than zero, then the patient airflow signal is understood to define a hump on the left side of the waveform, i.e., an obstruction that is pronounced in the initial phases of patient inspiration. If $\theta_d$ is greater than zero, then the patient airflow is understood to define a hump on the right side of the waveform, i.e., an obstruction that is pronounced in the later phases of patient inspiration.

Figure 4A:
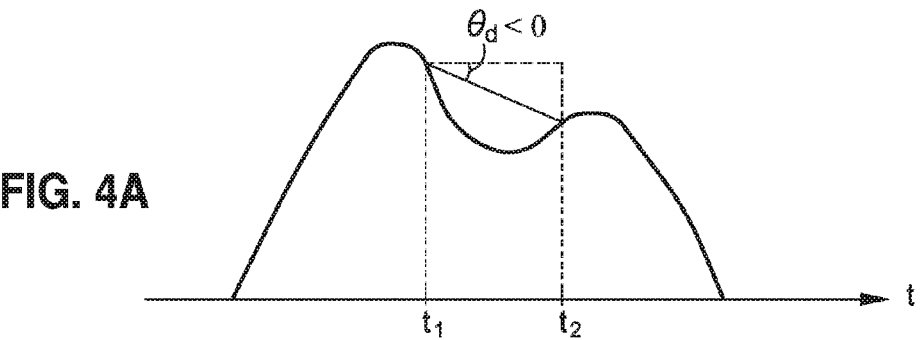
FIG. 4A-4C are graphs plotting various onsets of flow limitation.
Figure 4B:
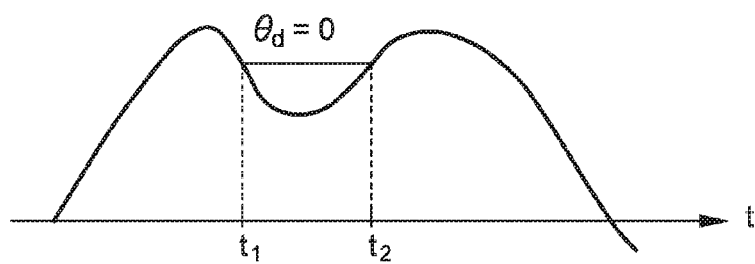
Figure 4C:
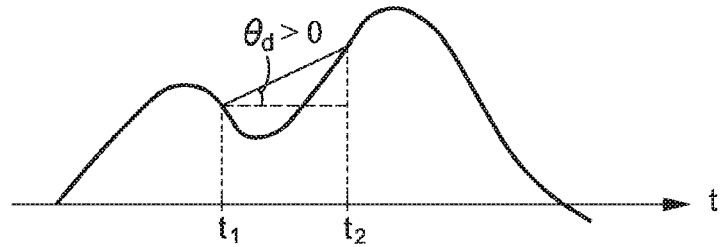

The graphs of FIG. 4A-4C illustrate the various onsets of flow limitation that result in different values of $\theta_d$. FIG. 4A in particular depicts a patient inspiration that exhibits flow limitation in which the peak flow is greater towards the beginning of inspiration than toward the end of inspiration. In this regard, the onset of flow limitation is understood to occur at a later time in the inspiration cycle. Deriving $\theta_d$ from the same airflow magnitudes at $t_1$ and $t_2$ from the above example, which corresponds to the zero crossings of the second derivative of the patient gas delivery signal, $t_1$ is understood to have a higher value than $t_2$. As such, $\theta_d$ is understood to be less than zero. The graph of FIG. 4B marks the same $t_1$ and $t_2$ instances as above, and because the peaks are symmetrical, the airflow magnitude at such instances are understood to be substantially the same. Accordingly, $\theta_d$ is approximately zero. The graph of FIG. 4C illustrates the patient gas delivery signal with the peak flow later on in the inspiration cycle, meaning that the flow limitation onset is toward the beginning. The values of $t_1$ and $t_2$ are the same as before, though the airflow magnitude at $t_1$ is understood to be less than the airflow magnitude at $t_2$. Based on this case, $\theta_d$ has a positive value, which, as indicated above, represents a hump or peak toward the end of the inspiration cycle.

The particulars shown herein are by way of example and for purposes of illustrative discussion of the embodiments of the disclosure only and are presented in the cause of providing what is believed to be the most useful and readily understood description of the principles and conceptual aspects of flow limitation detection. In this regard, no attempt is made to show details with more particularity than is necessary for the fundamental understanding of the present disclosure, the description taken with the drawings making apparent to those skilled in the art how the several forms of the present disclosure may be embodied in practice.

What is claimed is:

1. A method for identifying a flow limitation in a single inspiration respiratory cycle, the method comprising:
   delivering a flow of therapeutic breathing gas to a patient via a patient ventilation interface in pneumatic communication with a ventilation source over a gas conduit;
   receiving a patient gas delivery signal, the patient gas delivery signal being based on measurements of pressure differential between a first pressure sensor in pneumatic communication with the ventilation source and a second pressure sensor in pneumatic communication with the ventilation interface, the patient gas delivery signal being representative of a measure of therapeutic breathing gas being delivered to a patient airway at a given time instant and spanning the single inspiration respiratory cycle;
   generating a second derivative of the patient gas delivery signal;
   counting a total number of zero crossings in the generated second derivative of the patient gas delivery signal, the zero crossings of the second derivative of the patient gas delivery signal being representative of an inflection change in the patient gas delivery signal;
   generating a flow limitation indication corresponding to an identified flow limitation if the total number of zero crossings in the generated second derivative of the patient gas delivery signal is at least two;
   if a flow limitation indication is generated, determining an angle of deformation based upon a first gas delivery value corresponding to a first time instant of a first one of the zero crossings in the generated second derivative of the patient gas delivery signal and a second gas delivery value corresponding to a second time instant of a second one of the zero crossings in the generated second derivative of the patient gas delivery signal; and
   adjusting the flow of therapeutic breathing gas to the patient based upon the flow limitation indication and the determined angle of deformation.

2. The method of claim 1, wherein when the angle of deformation is approximately zero, the identified flow limitation is classified as symmetrical.

3. The method of claim 1, wherein the angle of deformation is less than zero, the identified flow limitation is classified as being pronounced in the initial phases of patient inspiration.

4. The method of claim 1, wherein the angle of deformation is greater than zero, the identified flow limitation is classified as being pronounced in the later phases of patient inspiration.

5. The method of claim 1, further comprising:
   retrieving a patient treatment action corresponding to a specific classification of the identified flow limitation as defined by the angle of deformation.

6. A respiratory assistance device, comprising:
   a variable speed blower with an output;
   a patient ventilation interface configured for fitment on a patient respiratory passageway;
   a first gas passage conduit coupling the output of the variable speed blower to the patient ventilation interface;
   a first pressure sensor for measuring a blower pressure at the output of the blower;
   a second pressure sensor for measuring a mask pressure in the patient ventilation interface; and
   a controller, in communication with the first sensor and the second sensor, that generates a patient gas delivery signal based on measurements of pressure differential between the first pressure sensor and the second pressure sensor, wherein a flow limitation indication is generated by the controller in response to a detection of at least two zero crossings in a second derivative of a single inspiration cycle of the patient gas delivery signal, the at least two zero crossings being representative of an inflection change in the patient gas delivery signal, and wherein, if a flow limitation indication is generated, determining on the controller an angle of deformation based upon a first as delivery value corresponding to a first time instant of a first one of the zero crossings in the second derivative of the single inspiration cycle of the patient gas delivery signal and a second gas delivery value corresponding to a second time instant of a second one of the zero crossings in the second derivative of the single inspiration cycle of the patient gas delivery signal.

7. The respiratory assistance device of claim 6, wherein when a flow limitation indication is generated the controller modifies operation of the variable speed blower in response to the flow limitation indication and the determined angle of deformation.

8. An article of manufacture comprising a tangible program storage medium readable by a data processing apparatus, the medium tangibly embodying one or more programs of instructions executable by the data processing apparatus to perform a method for identifying a flow limitation in a single inspiration respiratory cycle, the method comprising:

receiving a patient gas delivery signal, the patient gas delivery signal being based on measurements of pressure differential between a first pressure sensor in pneumatic communication with a ventilation source and a second pressure sensor in pneumatic communication with a ventilation interface to a patient airway, the patient gas delivery signal being representative of a measure of therapeutic gas being delivered to the patient airway at a given time instant and spanning the single inspiration respiratory cycle;

generating a second derivative of the patient gas delivery signal;

counting a total number of zero crossings in the generated second derivative of the patient gas delivery signal, the zero crossings of the second derivative of the patient gas delivery signal being representative of an inflection change in the patient gas delivery signal; and generating a flow limitation indication corresponding to an identified flow limitation if the total number of zero crossings in the generated second derivative of the patient gas delivery signal is at least two;

if a flow limitation indication is generated, determining an angle of deformation based upon a first gas delivery value corresponding to a first time instant of a first one of the zero crossings in the generated second derivative of the patient gas delivery signal and a second gas delivery value corresponding to a second time instant of a second one of the zero crossings in the generated second derivative of the patient gas delivery signal.

9. The article of manufacture of claim 8, wherein the method further comprises:

retrieving a patient treatment action corresponding to a specific classification of the identified flow limitation as defined by the determined angle of deformation.

* * * * *